United States Patent [19]
Stoss et al.

[11] 3,953,464
[45] Apr. 27, 1976

[54] CYCLIC SULPHOXIMIDES

[75] Inventors: Peter Stoss, Wildtal; Gerhard Satzinger, Denzlingen; Manfred Herrmann, St. Peter, all of Germany

[73] Assignee: Warner-Lambert Company, Morris Plains, N.J.

[22] Filed: Aug. 9, 1974

[21] Appl. No.: 495,985

[30] Foreign Application Priority Data
Aug. 11, 1973 Germany............................ 2340784
Mar. 11, 1974 Germany............................ 2411612

[52] U.S. Cl. ............................ 260/302 F; 424/246
[51] Int. Cl.²....................................... C07D 275/04

[58] Field of Search............. 260/304 I, 302, 304 A

[56] References Cited
OTHER PUBLICATIONS
Chem. Berichte, 1970, Vol. 103, pp. 3166–3181

Primary Examiner—Dale R. Ore
Attorney, Agent, or Firm—Albert H. Graddis; Frank S. Chow; George M. Yahwak

[57] ABSTRACT

The present invention is concerned with new cyclic sulphoximide derivatives with valuable pharmacological properties and with the preparation thereof.

22 Claims, No Drawings

CYCLIC SULPHOXIMIDES

The cyclic sulphoximides have previously not been investigated to any great extent. The known compounds of this type include a few 5-membered cyclic sulphoximides (See German Patent No. 1,914,016; Angew. Chem., 83: 83, 1971; J.A.C.S., 93: 7333, 1971; and J. Org. Chem., 38: 20, 1973) but the compounds described therein do not contain any functional groups so that they are not capable of modification by substitution or other reactions.

According to the present invention, there are provided new cyclic sulphoximide derivatives of the general formula:

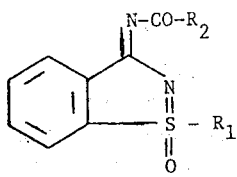

wherein $R_1$ is a lower alkyl or phenyl radical and $R_2$ is a phenoxy, lower alkoxy, lower alkoxyalkoxy, cycloalkoxy or lower alkyl radical or a phenyl radical optionally substituted by halogen atoms or hydroxyl groups or lower alkoxy radicals, or a lower phenylalkyl or phenoxyalkyl radical, the nucleus of which can be substituted or a hydroxyphenyl radical O-acylated with at least one lower aliphatic acyl radical.

Surprisingly, we have found that these new compounds (I) possess novel and valuable pharmacological properties. In particular, they possess a remarkable anti-inflammatory and analgesic activity, and yet have a very low toxicity. In contradistinction, the known sulphoximides have a completely different spectrum of activity.

By lower alkyl and alkoxy radicals, there is meant to be understood radicals containing up to 6, and preferably up to 4, carbon atoms in a straight or branched chain, for example, methyl, ethyl, n-propyl, isopropyl, n-butyl, sec.-butyl, pentyl and hexyl radicals and the oxy analogues thereof. As halogens, according to the present invention there are to be understood fluorine, chlorine and bromine, chlorine being preferred.

Preferred compounds of general formula (I) are those in which $R_1$ is a methyl or phenyl radical and $R_2$ is a straight-chained or branched alkyl or alkoxy radical containing up to 4 carbon atoms, a cycloalkoxy radical containing 5 to 7 carbon atoms, preferably a cyclohexoxy radical, an alkoxyalkoxy radical containing 2 to 6 carbon atoms, preferably a methoxyethoxy radical, a phenoxy radical or a phenyl, benzyl or phenoxymethyl radical optionally substituted by a halogen atom, preferably a chlorine atom, or a hydroxyl group or a methoxy radical, or an acetoxyphenyl radical.

The new compounds (I) according to the present invention can be prepared for example by reacting a 3H-3-imino-1,2-benzisothiazole-1-oxide of the general formula:

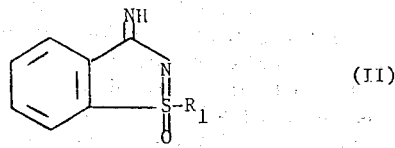

wherein $R_1$ has the same meaning as above, with a reactive derivative of an acid of the general formula:

$$R_2-COOH \qquad (III)$$

wherein $R_2$ has the same meaning as above.

As reactive derivatives of the acids (III), there are generally preferred those which have a sufficient activity towards the imino group; this applies, for example, to acid anhydrides and acid halides, especially acid chlorides, and to haloformic and halocarbonic acid esters.

The reaction of the compounds (II) with the derivatives of the acids (III) is usually carried out in an appropriate solvent which is inert under the reaction conditions, for example, benzene, toluene, xylenes, chloroform, dichloromethane, ethers, tetrahydrofuran, dioxan, acetone and the like. If desired, acid acceptors can be added, for example tertiary amines, such as triethylamine or pyridine, or basic inorganic compounds, such as potassium carbonate.

The reaction can be carried out at temperatures between about 0° and 100°C. and preferably at the boiling temperature of the selected solvent, under reflux.

The 3H-3-imino-1,2-benzisothiazole-1-oxides of general formula (II) used as starting material can be prepared, as disclosed in U.S. Ser. No. 495,984, filed Aug. 9, 1974. in the names of Satzinger and Stoss by reacting a compound of the general formula:

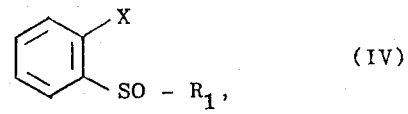

wherein $R_1$ has the same meaning as above and X is a nitril or amido group, with hydrazoic acid or a salt thereof in the presence of a strong acid. The compounds (II) thus obtained are then isolated by known procedures and, if desired, converted into a salt of an inorganic or organic acid.

As strong acids, there can be used, for example, sulphuric acid, phosphoric acid or preferably polyphosphoric acid or a mixture of phosphoric acid and phosphorus pentoxide.

The reaction of the compounds (IV) can be carried out at a temperature of between about 50° and 150°C. and preferably at 80° to 100°C.

Since the strong acid used in the reaction can also liberate hydrazoic acid from salts thereof, it is generally preferred to use the alkali metal or alkaline earth metal salts of hydroazoic acid, which are easier to handle.

The compounds of general formula (II) can either be isolated as salts of the acid used for the reaction or in the form of the free base and, as such, converted into salts by the addition of acids, for example, hydrochloric acid, hydrobromic acid, acetic acid, oxalic acid, salicylic acid, succinic acid, malic acid or the like.

The compounds of general formula (IV) in which X is an amido group are also new. They can be obtained, for example, by the oxidation of the corresponding sulphides by means of appropriate oxidation agents, for example, periodates, hydrogen peroxide, potassium permanganate, lead tetraacetate or the like.

The new compounds (I) according to the present invention can be administered enterally or parenterally in admixture with a solid or liquid pharmaceutical diluent or carrier. As injection medium, it is preferred to use water which contains the stabilisation agents, solubilising agents and buffers conventional for injection solutions. Additives of this type include, for example, tartrate and citrate buffers, ethanol, complex-forming agents (such as ethylenediamine-tetraacetic acid and the non-toxic salts thereof) and high molecular weight polymers (such as liquid polyethylene oxide) for viscosity regulation. Solid carrier materials include, for example starch, lactose, mannitol, methyl cellulose, talc, highly-dispersed silicic acids, high molecular weight fatty acids (such as stearic acid), gelatine, agar-agar, calcium phosphate, magnesium stearate, animal and vegetable fats and solid high molecular weight polymers (such as polyethylene glycols); compositions suitable for oral administration can, if desired, contain flavouring and sweetening agents.

The new compounds according to the present invention can be administered orally in dosage units of 10 to 500 mg. For parenteral administration, it is recommended to use dosage units of 5 to 100 mg.

The following Examples are given for the purpose of illustrating the present invention:

EXAMPLE 1

3-imino-1-methyl-3H-1,2-benzisothiazole-1-oxide

1. A solution of 184 g. sodium periodate in 1.7 liters water is added dropwise, while stirring, to a solution of 126 g. 2-methylthiobenzamide in 4 liters methanol and the reaction mixture than stirred for 24 hours. The precipitated sodium iodate is filtered off with suction and adhering reaction product is removed therefrom by washing with methanol. The bulk of the methanol is evaporated off from the filtrate in a vacuum, the greater part of the reaction product thereby crystallising out. This is filtered off with suction and the aqueous filtrate is continuously extracted with ethyl acetate. The residue of the extract, together with the quantity of reaction product previously obtained by suction filtration, are recrystallised from isopropanol. There is thus obtained pure 2-methyl-sulphinylbenzamide in the form of colourless needles; m.p. 192° – 193°C.

2. A mixture of 150 g. phosphoric acid, 100 g. phosphorus pentoxide and 36.6 g. 2-methylsulphinylbenzamide is heated to 90°C. While stirring, 26 g. sodium azide are added thereto portionwise in the course of an hour. Thereafter, the reaction mixture is stirred for a further 4 hours at 95°C., then cooled and the reaction mixture rendered alkaline with a saturated aqueous solution of potassium hydroxide. By shaking out with chloroform, there is obtained 3H-3-imino-1-methyl-1,2-benzisothiazole-1-oxide in the form of an oily residue which, upon rubbing, solidifies in the form of crystals. After recrystallisation from ethyl acetate, the product is obtained in the form of pale yellow crystals; m.p. 125°C.

The compound can be converted into its hydrochloride by reaction with hydrogen chloride in isopropanol. After recrystallisation from ethanol, this hydrochloride is obtained in the form of colourless crystals which melt, with decomposition, at 186°C.

EXAMPLE 2

3-imino-1-phenyl-1,2-benzisothiazole-1-oxide

This compound is prepared from 2-phenylthiobenzamide, in a manner analogous to that described in Example 1, by reaction with perhydrol (hydrogen peroxide) and ring closure of the 2-phenylsulphinylbenzamide obtained (m.p. 213°C.) by means of hydrazoic acid to give 3H-3-imino-1-phenyl-1,2-benzisothiazole-1-oxide; m.p. 178°C.

EXAMPLE 3

3-imino-1-phenyl-3H-1,2-benzisothiazole-1-oxide

This compound is prepared, in a manner analogous to that described in Example 1, from 2-phenyl-thiobenzamide by reaction with perhydrol and ring closure of the 2-phenylsulphinylbenzamide (m.p. 213°C.) thus obtained by reaction with hydrazoic acid to give 3-imino-1-phenyl-3H-1,2-benzisothiazole-1-oxide, which has a melting point of 178°C.

EXAMPLE 4

3-(Phenoxy-carbonylimino)-1-methyl-3H-1,2-benzisothiazole-1-oxide.

3.6 g. 3-imino-1-methyl-3H-1,2-benzisothiazole-1-oxide and 2.2 g. triethylamine are dissolved in 75 cc. chloroform. While stirring, there is added dropwise a solution of 3.1 g. phenyl chloroformate in 10 cc. chloroform. The reaction mixture is stirred for an hour, whereafter the chloroform solution is washed with dilute hydrochloric acid and then with water and subsequently dried over anhydrous sodium sulphate and evaporated. The residue is recrystallised from isopropanol/ethanol. There are obtained 4.8 g. 3-(phenoxy-carbonylimino)-1-methyl-3H-1,2-benzisothiazole-1-oxide; m.p. 138° – 139°C.

EXAMPLE 5

3-(Acetylimino)-1-phenyl-3H-1,2-benzisothiazole-1-oxide.

1.2 g. 3-imino-1-phenyl-3H-1,2-benzisothiazole-1-oxide are heated under reflux for 15 minutes with 0.4 g. acetyl chloride and 0.7 g. triethylamine in dioxan. Thereafter, the reaction mixture is poured into water and the precipitate obtained is filtered off with suction and recrystallised from ethyl acetate. There is thus obtained 3-(acetylimino)-1-phenyl-3H-1,2-benzisothiazole-1-oxide; m.p. 119°C.

EXAMPLE 6

3-(Propionylimino)-1-phenyl-3H-1,2-benzisothiazole-1-oxide.

From 12 g. 3-imino-1-phenyl-3H-1,2-benzisothiazole-1-oxide, 5 g. propionyl chloride and 6.6 g. triethylamine in chloroform, there is obtained, after heating under reflux for 3 hours and then working up the reaction mixture in the usual manner, the desired 3-(propionyl-imino)-1-phenyl-3H-1,2-benzisothiazole-1-oxide which, after recrystallisation from ethyl acetate, melts at 170°C.

EXAMPLE 7

3-(Isobutyrylimino)-1-phenyl-3H-1,2-benzisothiazole-1-oxide.

1.2 g. 3-imino-1-phenyl-3H-1,2-benzisothiazole-1-oxide is reacted with 0.5 g. isobutyric acid chloride and 0.7 g. triethylamine in chloroform in a manner analogous to that described in Example 6. There is thus obtained 3-(isobutyrylimino)-1-phenyl-3H-1,2-benzisothiazole-1-oxide which, after recrystallisation from ethyl acetate/diisopropyl ether, melts at 122°C.

EXAMPLE 8

3-(Salicyloylimino)-1-methyl-3H-1,2-benzisothiazole-1-oxide.

A solution of 1.6 g. salicylic acid chloride in 5 cc. tetrahydrofuran is added dropwise, while stirring, to a solution of 1.8 g. 3-imino-1-methyl-3H-1,2-benzisothiazole-1-oxide and 1.2 g. triethylamine in 50 cc. tetrahydrofuran. The reaction mixture is stirred overnight at ambient temperature, thereafter poured into water and the precipitate obtained is filtered off with suction. There is thus obtained 3-(salicyloylimino)-1-methyl-3H-1,2-benzisothiazole-1-oxide which, after recrystallisation from ethanol, melts at 168° – 169°C.

EXAMPLE 9

3-(3'-Methoxybenzoylimino)-1-phenyl-3H-1,2-benzisothiazole-1-oxide.

1.2 g. 3-imino-1-phenyl-3H-1,2-benzisothiazole-1-oxide, 0.7 g. triethylamine and 0.9 g. 3-methoxybenzoyl chloride are heated under reflux for 3 hours in 30 cc. dichloromethane and the reaction mixture then worked up in the manner described in Example 4. There is thus obtained 3-(3'-methoxybenzoylimino)-1-phenyl-3H-1,2-benzisothiazole-1-oxide which, after recrystallisation from ethyl acetate/diisopropyl ether, melts at 134°C.

EXAMPLE 10

3-(4'-Chlorobenzoylimino)-1-methyl-3H-1,2-benzisothiazole-1-oxide.

3.6 g. 3-imino-1-methyl-3H-1,2-benzisothiazole-1-oxide are reacted with 3.85 g. 4-chlorobenzoyl chloride and 2.3 g. triethylamine in chloroform in a manner analogous to that described in Example 6. There is thus obtained 3-(4'-chlorobenzoylimino)-1-methyl-3H-1,2-benzisothiazole-1-oxide which, after recrystallisation from isopropanol, melts at 170°C.

EXAMPLE 11

3-(Methoxycarbonylimino)-1-methyl-3H-1,2-benzisothiazole-1-oxide.

3.6 g. 3-imino-1-methyl-3H-1,2-benzisothiazole-1-oxide, 2 g. methyl chloroformate and 2.2 g. triethylamine are reacted in a manner analogous to that described in Example 4, the reaction time being 1 hour. There is thus obtained 3-(methoxycarbonylimino)-1-methyl-3H-1,2-benzisothiazole-1-oxide which, after recrystallisation from isopropanol, melts at 166°C.

EXAMPLE 12

3-(Ethoxycarbonylimino)-1-phenyl-3H-1,2-benzisothiazole-1-oxide.

12 g. 3-imino-1-phenyl-3H-1,2-benzisothiazole-1-oxide are reacted with 5.5 g. ethyl chloroformate and 6.6 g. triethylamine in chloroform in a manner analogous to that described in Example 4. There is thus obtained 3-(ethoxycarbonylimino)-1-phenyl-3H-1,2-benzisothiazole-1-oxide which, after recrystallisation from methanol, melts at 163°C.

EXAMPLE 13

3-(sec.-Butoxycarbonylimino)-1-methyl-3H-1,2-benzisothiazole-1-oxide.

9 g. 3-imino-1-methyl-3H-1,2-benzisothiazole are reacted with 6 g. triethylamine and 7.5 g. sec.-butyl chloroformate in a manner analogous to that described in Example 4. There is thus obtained 3-(sec.-butoxycarbonylimino)-1-methyl-3H-1,2-benzisothiazole-1-oxide which, after recrystallisation from isopropanol, melts at 125°C.

EXAMPLE 14

3-(Phenoxycarbonylimino)-1-phenyl-3H-1,2-benzisothiazole-1-oxide.

12 g. 3-imino-1-phenyl-3H-1,2-benzisothiazole-1-oxide are reacted with 8 g. phenyl chloroformate and 6.6 g. triethylamine in a manner analogous to that described in Example 4. There is thus obtained 3-(phenoxycarbonylimino)-1-phenyl-3H-1,2-benzisothiazole-1-oxide which, after recrystallisation from methanol, melts at 173°C.

EXAMPLE 15

3-[(2-Methoxyethoxy)-carbonylimino]-1-methyl-3H-1,2-benzisothiazole-1-oxide.

A solution of 7.2 g. 3-imino-1-methyl-3H-1,2-benzisothiazole-1-oxide in 200 cc. acetone is mixed with 22 g. anhydrous potassium carbonate. 7 g. ethyl 2-methoxyethyl-chlorocarbonate in 50 cc. acetone are added dropwise thereto. After 30 minutes, the reaction mixture is poured into ice-water and extracted with chloroform and the extract then evaporated. The residue is recrystallised from isopropanol to give 3-[(2-methoxyethoxy)-carbonylimino]-1-methyl-3H-1,2-benzisothiazole-1-oxide, which melts at 108° – 109°C.

EXAMPLE 16

3-(4-Chlorophenoxyacetylimino)-1-phenyl-3H-1,2-benzisothiazole-1-oxide.

24 g. 3-imino-1-phenyl-3H-1,2-benzisothiazole-1-oxide, 13.2 g. triethylamine and 21 g. 4-chlorophenoxyacetyl chloride are heated under reflux for 1 hour in 1 liter chloroform. After working up the reaction mixture in the usual manner, there is obtained 3-(4-chlorophenoxyacetylimino)-1-phenyl-3H-1,2-benzisothiazole-1-oxide which, after recrystallisation from acetonitrile, is obtained in the form of colourless, felted needles melting at 196°C.

EXAMPLE 17

3-(Phenylacetylimino)-1-phenyl-3H-1,2-benzisothiazole-1-oxide.

2.4 g. 3-imino-1-phenyl-3H-1,2-benzisothiazole-1-oxide are boiled for 1 hour with 1.32 g. triethylamine and 1.6 g. phenylacetyl chloride in 50 cc. chloroform. After working up in the usual manner, there is obtained 3-(phenylacetylimino)-1-phenyl-3H-1,2-benzisothiazole-1-oxide in the form of yellow crystals which, after recrystallisation from ethyl acetate, melt at 120°C.

EXAMPLE 18

3-(Cyclohexyloxycarbonylimino)-1-methyl-3H-1,2-benzisothiazole-1-oxide.

7.2 g. 3-imino-1-methyl-3H-1,2-benzisothiazole-1-oxide, 22 g. potassium carbonate and 7.8 g. cyclohexyl chlorocarbonate are reacted in 200 cc. acetone in the manner described in Example 15. There is thus obtained 3-(cyclohexyloxycarbonylimino)-1-methyl-3H-1,2-benzisothiazole-1-oxide which, after recrystallisation from isopropanol, melts at 126° – 128°C.

EXAMPLE 19

3-(Acetylsalicyloylimino)-1-phenyl-3H-1,2-benzisothiazole-1-oxide.

2.4 g. 3-imino-1-phenyl-3H-1,2-benzisothiazole-1-oxide are boiled for 1 hour with 2 g. acetyl-salicylic acid and 1.32 g. triethylamine in 100 cc. chloroform. After working up in the usual manner, there is obtained 3-(acetylsalicyloylimino)-1-phenyl-3H-1,2-benzisothiazole-1-oxide in the form of colourless crystals which, after recrystallisation from ethyl acetate, melts at 160°C. Structurally, the compounds of this invention are:

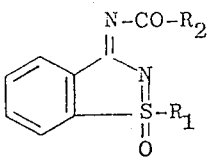

| Example | $R_1$ | $R_2$ | salt | melting point (°C) |
|---|---|---|---|---|
| 4 | methyl | phenoxy | — | 138–139 |
| 5 | phenyl | methyl | — | 119 |
| 6 | phenyl | ethyl | — | 170 |
| 7 | phenyl | iso-propyl | — | 122 |
| 8 | methyl | ⌬-OH | — | 168–169 |
| 9 | phenyl | ⌬-OCH₃ | — | 134 |
| 10 | methyl | ⌬-Cl | — | 170 |
| 11 | methyl | methoxy | — | 166 |
| 12 | phenyl | ethoxy | — | 163 |
| 13 | methyl | butoxy-2 | — | 125 |
| 14 | phenyl | phenoxy | — | 173 |
| 15 | methyl | —O—CH₂—CH₂—OCH₃ | — | 108–190 |
| 16 | phenyl | —CH₂—O—C₆H₄—Cl(r) | — | 196 |
| 17 | phenyl | —CH₂—C₆H₅ | — | 120 |
| 18 | methyl | —O—C₆H₁₁ | — | 126–128 |
| 19 | phenyl | —C₆H₄—O—CO—CH₃(o) | — | 160 |

Pharmacologic activity of the compounds of the present invention following conventional well-recognized procedures showed the following:

| Example | $LD_{50}$ | Activity |
|---|---|---|
| 12 | 1600 mg/kg ig. | 250 mg/kg antiphlogistic |
| 7 | 600 mg/kg ig. | 100 mg/kg i.g. antisecretory (Shay Rat) |
| 8 | 1600 mg/kg. i.g. | Guinea pig cough (Antitussive) 250 mg/kg equivalent to 150 mg/kg codeine |
| 6 | 1600 mg/kg. i.g. | Antiphlogistic and analgesic |

We claim:

1. Cyclic sulphoximide of the formula:

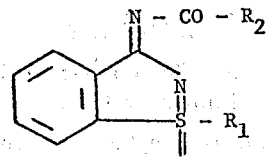

wherein $R_1$ is methyl or phenyl and $R_2$ is alkyl or alkoxy containing up to 4 carbon atoms, cyclohexoxy, methoxyethoxy, phenoxy, phenyl, benzyl, phenoxymethyl which may be substituted by chlorine atom, hydroxy group or methoxy, or acetoxyphenyl.

2. Cyclic sulphoximide of the formula:

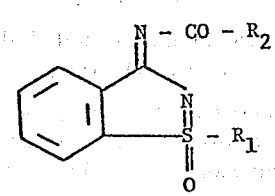

wherein
  $R_1$ is methyl or phenyl;
  $R_2$ is methyl, methoxy, ethyl, ethoxy, isopropyl, butoxy, phenoxy, methoxyethoxy, chlorophenoxymethylene, benzyl, hexyloxy, (methylcarboxy) phenyl, m-methoxyphenyl, o-hydroxyphenyl, and p-chlorophenyl.

3. The cyclic sulphoximide of claim 2 wherein $R_1$ is methyl.

4. The cyclic sulphoximide of claim 3 which is 3-(Methoxycarbonylimino)-1-methyl-3H-1,2-benzisothiazole-1-oxide.

5. The cyclic sulphoximide of claim 3 which is 3-(sec.-Butoxycarbonylimino)-1-methyl-3H-1,2-benzisothiazole-1-oxide.

6. The cyclic sulphoximide of claim 3 which is 3-[(2-Methoxyethoxy)carbonylimino]-1-methyl-3H-1,2-benzisothiazole-1-oxide.

7. The cyclic sulphoximide of claim 3 which is 3-(Cyclohexyloxycarbonylimino)-1-methyl-3H-1,2-benzisothiazole-1-oxide.

8. The cyclic sulphoximide of claim 3 which is 3-(4'-Chlorobenzoylimino)-1-methyl-3H-1,2-benzisothiazole-1-oxide.

9. The cyclic sulphoximide of claim 3 which is 3-(Salicylolimino)-1-methyl-3H-1,2-benzisothiazole-1-oxide.

10. The cyclic sulphoximide of claim 3 which is 3-(Phenoxycarbonylimino)-1-methyl-3H-1,2-benzisothiazole-1-oxide.

11. The cyclic sulphoximide of claim 2 wherein $R_1$ is phenyl.

12. The cyclic sulphoximide of claim 11 which is 3-(Acetylimino-1-phenyl-3H-1,2-benzisothiazole-1-oxide.

13. The cyclic sulphoximide of claim 11 which is 3-(Propionylimino)-1-phenyl-3H-1,2-benzisothiazole-1-oxide.

14. The cyclic sulphoximide of claim 11 which is 3-(Isobutyrylimino)-1-phenyl-3H-1,2-benzisothiazole-1-oxide.

15. The cyclic sulphoximide of claim 11 which is 3-(3'-Methoxybenzoylimino)-1-phenyl-3H-1,2-benzisothiazole-1-oxide.

16. The cyclic sulphoximide of claim 11 which is 3-(Ethoxycarbonylimino)-1-phenyl-3H-1,2-benzisothiazole-1-oxide.

17. The cyclic sulphoximide of claim 11 which is 3-(Phenoxycarbonylimino)-1-phenyl-3H-1,2-benzisothiazole-1-oxide.

18. The cyclic sulphoximide of claim 11 which is 3-(4-Chlorophenoxyacetylimino)-1-phenyl-3H-1,2-benzisothiazole-1-oxide.

19. The cyclic sulphoximide of claim 11 which is 3-(Phenylacetylimino)-1-phenyl-3H-1,2-benzisothiazole-1-oxide.

20. The cyclic sulphoximide of claim 11 which is 3-(Acetylsalicyloylimino)-1-phenyl-3H-1,2-benzisothiazole-1-oxide.

21. A process for the preparation of the cyclic sulphoximide of claim 2 wherein a 3-H-3-imino-1,2-benzisothiazole-1-oxide of the formula:

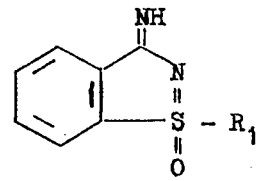

in which $R_1$ is methyl or phenyl, is reacted at a temperature between about 0 and 100°C in an inert solvent with an acid halide or acid anhydride of the formula:

$R_2COOH$ in which $R_2$ is methyl, methoxy, ethyl, ethoxy, isopropyl, butoxy, phenoxy, methoxyethoxy, chlorophenoxymethylene, benzyl, hexyloxy, (methylcarboxy)phenyl, m-methoxyphenyl, 0-hydroxyphenyl, and p-chlorophenyl.

22. The process according to claim 21 wherein the reaction is carried out in the presence of a tertiary amine as acid acceptor.

* * * * *